United States Patent [19]

Gordon et al.

[11] Patent Number: 4,714,757
[45] Date of Patent: Dec. 22, 1987

[54] AMINOPEPTIDASE INHIBITORS

[75] Inventors: Eric M. Gordon, Pennington; Jollie D. Godfrey, Jr., Trenton; Norma G. Delaney, Princeton, all of N.J.

[73] Assignee: E. R. Squibb & Sons, Inc., Princeton, N.J.

[21] Appl. No.: 777,121

[22] Filed: Sep. 18, 1985

[51] Int. Cl.⁴ ...................... C07K 5/506; C07K 5/508
[52] U.S. Cl. .................................... 530/329; 530/330; 530/331; 530/332
[58] Field of Search ...................... 260/298.2; 530/331, 530/330, 329, 332

[56] References Cited

U.S. PATENT DOCUMENTS 4,636,560  1/1987  Godfrey, Jr. et al. ............. 530/331

FOREIGN PATENT DOCUMENTS 0200406  12/1986  European Pat. Off. .

OTHER PUBLICATIONS

Allinger et al, "Organic Chemistry", 1971, pp. 494-497, Worth Publishers.
Umezawa et al., J. Antibiotics, vol. 29, pp. 97-99 (1976).
Ocain et al., Ninth American Peptide Symposium, University of Toronto, Toronto, Ontario, Canada, Jun. 23-28, 1985.
Umezawa et al., J. Antibiotics, vol. 29, pp. 100-101 (1976).

*Primary Examiner*—Delbert R. Phillips
*Assistant Examiner*—Nathan M. Nutter

*Attorney, Agent, or Firm*—Lawrence S. Levinson; Donald J. Barrack

[57] ABSTRACT

Aminopeptidase inhibitory activity is exhibited by compounds having the formula

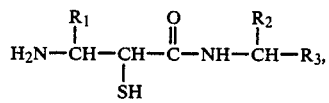

and pharmaceutically acceptable salts thereof, wherein
$R_1$ and $R_2$ are each independently hydrogen, alkyl, carboxyalkyl, halo-substituted alkyl, hydroxyalkyl, aminoalkyl, mercaptoalkyl, alkylthioalkyl, (cycloalkyl)alkyl, (heteroaryl)alkyl, arylalkyl, carbamoylalkyl, guanidinylalkyl or heteroaryl;
$R_3$ is hydrogen, alkyl, cycloalkyl, aryl, heteroaryl, arylalkyl, (heteroaryl)alkyl,

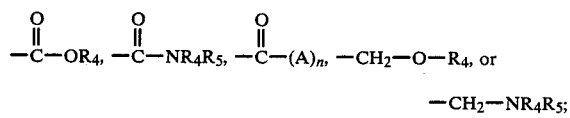

$R_4$ and $R_5$ are each independently hydrogen, alkyl, cycloalkyl, aryl, heteroaryl, arylalkyl, or (heteroaryl)alkyl;
A is glycyl, alanyl, leucyl, phenylalanyl, arginyl, sarcosyl, seryl, asparagyl, lysyl, glutamyl, histidyl, tryptophyl, cysteinyl, methionyl, threonyl, tyrosyl, valyl, aspartyl, prolyl, norleucyl, or norvalyl; and
n is an integer of 1 to 6.

9 Claims, No Drawings

AMINOPEPTIDASE INHIBITORS

BRIEF DESCRIPTION OF THE INVENTION

Compounds having the formula

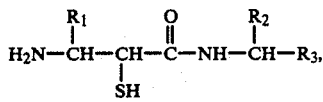

and pharmaceutically acceptable salts thereof, have aminopeptidase inhibitory activity, and can be used as analgesics. In formula I, and throughout the specification, the symbols are as defined below.

$R_1$ and $R_2$ are each independently hydrogen, alkyl, carboxyalkyl, halo-substituted alkyl, hydroxyalkyl, aminoalkyl, mercaptoalkyl, alkylthioalkyl, (cycloalkyl)alkyl, (heteroaryl)alkyl, arylalkyl, carbamoylalkyl, guanidinylalkyl or heteroaryl;

$R_3$ is hydrogen, alkyl, cycloalkyl, aryl, heteroaryl, arylalkyl, (heteroaryl)alkyl,

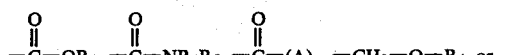

$R_4$ and $R_5$ are each independently hydrogen, alkyl, cycloalkyl, aryl, heteroaryl, arylalkyl, or (heteroaryl)alkyl;

A is glycyl, alanyl, leucyl, phenylalanyl, arginyl, sarcosyl, seryl, asparagyl, lysyl, glutamyl, histidyl, tryptophyl, cysteinyl, methionyl, threonyl, tyrosyl, valyl, aspartyl, prolyl, norleucyl, or norvalyl; and n is 0 or an integer of 1 to 6.

Listed below are definitions of various terms used to describe the compound of this invention. These definitions apply to the terms as they are used throughout the specification (unless they are otherwise limited in specific instances) either individually or as part of a larger group.

The terms "alkyl" and "alkoxy" refer to straight and branched chain groups having 1 to 7 carbon atoms.

The term "halo substituted alkyl" refers to alkyl groups in which one, or more, hydrogens have been replaced by chloro, bromo or fluoro groups. Exemplary groups are trifluoromethyl, which is preferred, pentafluoroethyl, 2,2,2-trichloroethyl, chloromethyl and bromomethyl.

The term "cycloalkyl" refers to cycloalkyl groups having 3, 4, 5, 6 or 7 carbon atoms.

The term "heteroaryl" refers to 2- or 3-furanyl, 2- or 3-thienyl, 2-, 3- or 4-pyridinyl, 4-imidazolyl and 3-indolyl.

The term "aryl" refers to phenyl and substituted phenyl. Phenyl groups substituted with 1, 2 or 3 alkyl, alkoxy, alkylthio, hydroxy, chlorine, bromine, fluorine, amino, alkylamino, dialkylamino, nitro or trifluoromethyl groups.

DETAILED DESCRIPTION OF THE INVENTION

The compounds of formula I, and the pharmaceutically acceptable salts thereof, can be administered to a mammalian specie (e.g., humans) as an analgesic agent due to their ability to inhibit an enkephalin-degrading aminopeptidase.

It is well known that the weak and short-lasting analgesic activity of endogenous enkephalins can be attributed to their rapid inactivation. Enkephalins are metabolized by several hydrolytic enzymes present in the brain: (1) aminopeptidases release the Tyr[1] residue, (2) a dipeptidyl aminopeptidase releases the Tyr[1]-Gly[2] residue and (3) two enzymes cleave the penultimate Gly[3]-Phe[4] bond to release an intact dipeptide fragment, angiotensin-converting enzyme, and a discrete enzyme commonly designated enkephalinase.

It has been suggested that both enkephalinase and an aminopeptidase activity (probably membrane-bound) play key roles in enkephalin metabolism. The compounds of this invention inhibit the amino-peptidase activity and thus act as analgesic agents.

A compound of formula I, or a pharmaceutically acceptable salt thereof, can be administered to patients orally or parenterally in an effective amount within the daily dosage range of about 0.1 to about 25 milligrams of compound per kilogram of patient body weight. Administration can be once daily or in 2 to 4 divided daily doses.

The compounds of this invention can be obtained by first treating an activated form (preferably a mixed anhydride) of an N-protected amino acid having the formula

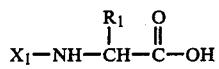

with diazomethane to yield a compound having the formula

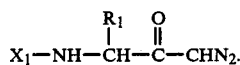

Treatment of a diazoketone of formula III in methanol with silver benzoate and triethylamine yields a compound having the formula

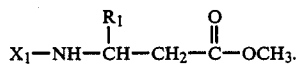

Treatment of a compound of formula IV with lithium diisopropylamide and a disulfide having the formula

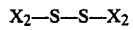

at a reduced temperature yields the corresponding compound having the formula

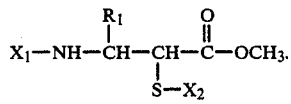

The ester of formula VI can be converted to the corresponding carboxylic acid having the formula

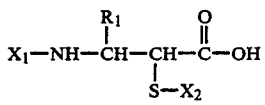

VII by treatment with a base (e.g., sodium hydroxide).

Coupling a compound of formula VII with a compound having the formula

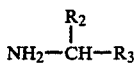

VIII is best accomplished by first activating the carboxylic acid of formula VII and then reacting the activated derivative with a compound of formula VIII. If the compound of formula VIII contains a reactive substituent (e.g., a carboxyl group) it should be protected prior to coupling with an activated derivative of a compound of formula VII. The product of the above coupling must be deprotected to obtain the desired product of formula I. Deprotection can be accomplished using art-recognized procedures which will, of course, depend on the particular protecting group.

The compounds of formula I form acid-addition salts with a variety of inorganic and organic acids. The pharmaceutically acceptable salts include, for example, the hydrohalides, e.g., hydrochloride, hydrobromide, etc., sulfate, phosphate, nitrate, arylsulfonate, (e.g., camphor-sulfonate, benzenesulfonate, toluenesulfonate, etc.), citrate, ascorbate, maleate, fumarate, pamoate, acetate, tartrate, salicylate and the like. It is frequently convenient to isolate the compound by forming the acid salt and precipating in a medium in which it is insoluble.

The compounds of formula I wherein $R_3$ is

and $R_4$ is hydrogen form basic salts with a variety of inorganic and organic bases. The pharmaceutically acceptable salts include alkali metal salts such as sodium or potassium, alkaline earth metal salts such as calcium or magnesium, and salts derived from amino acids such as arginine, lysine, etc. The salts can be prepared by reacting the acid form of the compound, i.e., $R_3$ is carboxyl, with an equivalent of the base supplying the desired basic ion in a medium in which the salt precipitates or in aqueous medium and then lyophilizing.

In the compounds of formula I, the carbon atom to which the mercapto group is attached is asymmetric, the carbon atom to which the $R_1$ substituent is attached will also be asymmetric if $R_1$ is other than hydrogen, and the carbon atom to which the $R_2$ and $R_3$ substituents are attached may also be asymmetric. The compounds, therefore, may exist in stereoisomeric forms, and as racemic mixtures thereof. All of these are within the scope of this invention. The above-described syntheses can utilize the racemate or one of the diastereomers as the starting material. When the racemic starting material is used in the synthetic procedure, the stereoisomers obtained in the product can be separated by conventional chromatographic or fractional crystallization techniques.

The following examples are specific embodiments of this invention.

EXAMPLE 1

N-[(3S)-3-Amino-2-mercapto-1-oxo-4-phenylbutyl]-L-leucine (A)

(S)-3-Diazo-2-oxo-1-(phenylmethyl)carbamic acid, 1,1-dimethyl ester

To a solution of N-(t-butoxycarbonyl)-L-phenylalanine (47.75 g, 0.18 mole) and N-methyl-morpholine (19.8 ml, 0.18 mole) in dry tetrahydrofuran (300 ml) at −20° C. under argon was added over a 5 minute period isobutyl chloroformate (23.4 ml, 0.18 mole). After stirring for 20 minutes at −20° C., the N-methylmorpholine hydrochloride was removed by filtration and the filter cake was washed with a small portion of cold tetrahydrofuran. The filtrate was treated with a cold (0° C.), ethereal solution of diazomethane (∼270 mmol, prepared from 64.2 g of Diazald and distilled). After stirring at 0° C. for 30 minutes, the mixture was warmed to room temperature. After stirring for 2.5 hours, the excess diazomethane was removed by bubbling a stream of argon through the reaction mixture for 1 hour. The bulk of the solvent was removed at reduced pressure and the residue was dissolved in ethyl acetate. The resulting solution was washed with water (twice), 0.25 M citric acid (twice), 1N sodium bicarbonate, and brine. After drying over anhydrous magnesium sulfate, the solvent was removed at reduced pressure and the residue was dissolved in isopropyl ether and placed in the cold (∼5° C.). The resulting crystals were collected by filtration and washed with hexane to give (S)-3-diazo-2-oxo-1-(phenylmethyl) carbamic acid, 1,1-dimethyl ester as a bright yellow solid: 33.96 g, $R_f$=0.21 (silica gel, hexane:ethyl acetate, 3:1). The mother liquors yielded an additional 7.45 g of (S)-3-diazo-2-oxo-1-(phenylmethyl)carbamic acid, 1,1-dimethyl ester.

(B)

(S)-3-[[(1,1-Dimethylethoxy)carbonyl]amino]-benzenebutanoic acid, methyl ester

To a solution of (S)-3-diazo-2-oxo-1-(phenylmethyl)-carbamic acid, 1,1-dimethyl ester (5.36 g, 18.52 mmol) in methanol (50 ml) was added 5.0 ml of a solution of silver benzoate (1.0 g) in triethylamine (10 ml). After nitrogen evolution had ceased, an additional 0.2 ml of the silver benzoate/triethylamine solution was added. After stirring for 15 minutes, the reaction mixture was treated with activated charcoal and filtered through Celite using ethyl acetate. The filtrate was concentrated at reduced pressure and the residue was dissolved in ethyl acetate and washed with water (twice), 1N sodium bicarbonate (twice), 1N hydrochloric acid (twice), 1N sodium bicarbonate and brine. After drying over anhydrous magnesium sulfate, the solvent was removed at reduced pressure and the residue chromatographed (flash, silica gel; benzene:isopropyl ether, 87.5:12.5) to give (S)-3-[[(1,1-dimethylethoxy)carbonyl]amino]benzenebutanoic acid, methyl ester as a colorless solid: 4.33 g; $[\alpha]_D^{20}$=−19.2° (c=1.06, methanol; $R_f$=0.31 (silica gel, benzene:ethyl acetate, 9:1).

(C)

(3S)-3-[[(1,1-Dimethylethoxy)carbonyl]amino]-2-[[(4-methoxyphenyl)methyl]thio]benzenebutanoic acid, methyl ester.

To a solution of freshly distilled diisopropylamine (2.10 ml, 15 mmol) in anhydrous tetrahydrofuran (20 ml) at 0° C. under argon was added a hexane solution of n-butyl lithium (6.10 ml of a 2.40 M solution, 14.65 mmol). After stirring at 0° C. for 30 minutes, the resulting solution of lithium diisopropylamide was cooled to −78° C. and a solution of (S)-3-[[(1,1-dimethylethoxy)carbonyl]amino]benzenebutanoic acid, methyl ester (2.0 g, 6.81 mmol) in dry tetrahydrofuran (8 ml) was added dropwise over a period of 5 minutes. After stirring at −78° C. for 15 minutes, a solution of p-methoxybenzyl disulfide (2.50 g, 8.18 mmol) in dry tetrahydrofuran (9 ml) was added. After 5 minutes at −78° C., the mixture was warmed to 0° C. and stirring continued for 45 minutes. The reaction was quenched with 1N hydrochloric acid and diluted with ethyl acetate. The resulting solution was washed with water, 1N hydrochloric acid, 1N sodium bicarbonate, and brine. After drying over anhydrous magnesium sulfate, the solvent was removed at reduced pressure and the residue chromatographed (flash, silica; benzene:isopropyl ether, 92:8) to give (3S)-3-[[(1,1-dimethylethoxy)carbonyl]amino]-2-[[(4-methoxyphenyl)methyl]thio]benzenebutanoic acid, methyl ester as a colorless oil: 1.89 g, $R_f$=0.54 (silica gel, benzene:isopropyl ether, 4:1).

(D)

(3S)-3-[[(1,1-Dimethylethoxy)carbonyl]amino]-2-[[(4-methoxyphenyl)methyl]thio]benzenebutanoic acid A mixture of (3S)-3-[[(1,1-dimethylethoxy)carbonyl]amino]-2-[[(4-methoxyphenyl)methyl]thio]benzenebutanoic acid, methyl ester (1.24 g, 2.78 mmol), 1N sodium hydroxide (8.4 ml, 3 eq), water (1.6 ml) and tetrahydrofuran (10 ml) was stirred at room temperature for 20 hours after which 1N sodium hydroxide (5 ml) was added. After 20 hours, the reaction was made acidic with the addition of 1N hydrochloric acid, diluted with ethyl acetate and the organic phase washed twice with water and brine. Drying over anhydrous magnesium sulfate and removal of solvent yielded the title compound as an amber oil (1.34 g).

(E)

N-[(3S)-[[(1,1-Dimethylethoxy)carbonyl]amino]-2-[[(4-methoxyphenyl)methyl]thio]-1-oxo-4-phenylbutyl-L-leucine, 1,1-dimethylethyl ester A solution of (3S)-3-[[(1,1-dimethylethoxy)carbonyl]amino]-2-[[(4-methoxyphenyl)methyl]thio]-benzenebutanoic acid (690 mg, 1.6 mmol) 2-morpholinoethyl isocyanide (0.22 ml, 1 eq), 1-hydroxybenzotriazole monohydrate (216 mg, 1 eq) and dry dichloromethane (10 ml) was stirred under argon for 45 minutes after which it was treated with a solution of L-leucine-t-butyl ester (300 mg, 1 eq) in dichloromethane (4 ml) followed by diisopropylethyl amine (0.33 ml, 1.2 eq). The resulting mixture was stirred 18 hours at room temperature. The reaction mixture was diluted with ethyl acetate and washed with water (twice), 1N hydrochloric acid (twice), 1N sodium hydroxide (twice) and brine, dried over anhydrous magnesium sulfate and concentrated to a yellow solid. The solid was chromatographed (flash, silica gel LPS-1, benzene: ethyl acetate 92:8) to yield the title compound as a colorless solid (460 mg, 0.78 mmol) TLC:$R_f$=0.25 Isomer B, $R_f$=0.31 Isomer A (silica gel, benzene: ethyl acetate 9:1).

(F)

N-[(3S)-3-Amino-2-mercapto-1-oxo-4-phenylbutyl]-L-leucine

A solution of N-[(3S)-[[(1,1-dimethylethoxy)-carbonyl]amino]-2-[[(4-methoxyphenyl)methyl]thio]-1-oxo-4-phenylbutyl-L-leucine, 1,1-dimethylethyl ester (638 mg, 1.06 mmol), trifluoroacetic acid (14 ml) and anisole (1.0 ml) was stirred under argon for 1 hour. The solution was cooled to 0° C. and treated with mercuric trifluoroacetate (498 mg, 1.1 eq) and stirring continued at 0° C. for 1 hour. The reaction was then concentrated to red oil, diluted with ether (10 ml) and hexane was added to form a colorless precipitate. The solid was triturated in the ether/hexane solution, collected by filtration, washed with hexane and dried under argon to yield a colorless solid. The solid was taken into 80% aqueous acetic acid (25 ml) and hydrogen sulfide was bubbled through the solution for 30 minutes. The black reaction mixture was filtered through a pad of Celite followed by a millipore filter (teflon). The filtrate was concentrated and the colorless residue diluted with degassed double distilled water (20 ml) and 1N hydrochloric acid (1.5 ml, 1.5 eq). The mixture was filtered (millipore, Metricel) and the clear, colorless filtrate was lyophilized twice to yield the title compound as a fluffy colorless solid (353 mg, 0.98 mmol), $R_f$=0.72 (silica gel, n-butanol:acetic acid:water, 4:1:1): $R_f$=0.61 Isomer A, $R_f$=0.46 Isomer B (silica gel, chloroform: methanol:acetic acid, 4:1:1); fast atom bombardment mass spectrum: (M+H)+m/e=325, (M−H)−m/e=323; $[\alpha]_D$=−20.4° (c=1.08, pyridine); $[\alpha]_{365}$=−76.8° (c=1.08, pyridine); melting point 96°–105° C.

Analysis Calc'd: $C_{16}H_{25}N_2O_3S \cdot 0.091$ mole trifluoroacetic acid·0.95 mole hydrochloric acid: C, 52.47; H, 7.08; N, 7.56; S, 8.65; SH, 8.93; Cl, 9.09; F, 1.40. Found: C, 52.47; H, 6.79; N, 7.05; S, 8.24; SH, 8.66; Cl, 9.04; F, 1.00.

EXAMPLE 2

N-[(3R)-3-Amino-2-mercapto-1-oxo-4-phenylbutyl]-L-leucine, monohydrochloride (Isomer A)

(A)

(R)-3-Diazo-2-oxo-1-(phenylmethyl)carbamic acid, 1,1-dimethylethyl ester

To a solution of N-(t-butoxycarbonyl)-D-phenylalanine (52.2 g, 0.1986 mol) and N-methylmorpholine (21.6 ml, 0.196 mol) in anhydrous tetrahydrofuran (300 ml) at −20° C. under argon was added, over a period of 5 minutes, isobutylchloroformate (25.4 ml, 0.196 mol). After stirring at −20° C. for 20 minutes, the mixture was filtered and the filter cake was washed with a small portion of cold ether. The filtrate was treated with a cold (−20° C.), ethereal solution of diazomethane (~270 mmol, prepared from 64.2 g of Diazald and distilled). After stirring at −20° C. to 0° C. for 30 minutes, the mixture was warmed to room temperature. After stirring for 2 hours, the excess diazomethane was removed by bubbling a stream of argon through the reaction mixture for 45 minutes. The bulk of the solvent was removed at reduced pressure and the residue was dissolved in ethyl acetate. The resulting solution was washed with water (twice), 0.25 M citric acid (twice), 1N sodium bicarbonate, and brine. After drying over anhydrous magnesium sulfate, the solvent was removed at reduced pressure to give a bright yellow oil which was dissolved in isopropyl ether and placed in the cold (5° C.). After standing overnight, the resulting crystals were collected by filtration and washed with hexane to afford the title compound as a yellow solid: 20.3 g; $R_f=0.29$ (silica gel; hexane:ethyl acetate, 7:3); $[\alpha]_{DD}^{20}=+35.2°$ (c=2.56, methanol). The mother liquors yielded an additional 8.08 g of product.

(B)

(R)-3-[[(1,1-Dimethylethoxy)carbonyl]amino]benzenebutanoic acid, methyl ester

A solution of silver benzoate (1.0 g) and triethylamine (20 ml) was prepared. To a stirring mixture of (R)-3-diazo-2-oxo-1-(phenylmethyl)carbamic acid, 1,1-dimethylethyl ester (10.0 g, 34.56 mmol) and methanol (100 ml) was added a portion of the silver benzoate/triethylamine solution (10 ml). After 20 minutes additional silver benzoate/triethylamine was added (5 ml) and stirring continued for 45 minutes. The dark reaction mixture was treated with Celite, decolorizing carbon and brine. The resulting mixture was filtered through Celite and the filtrate concentrated, diluted with ethyl acetate and washed with water (twice), 1N sodium bicarbonate (twice), 1N hydrochloric acid (twice), 1N sodium bicarbonate and brine, dried over anhydrous magnesium sulfate and concentrated to an amber oil. The oil was chromatographed (flash, silica gel LPS-1, benzene:isopropyl ether 85:15) to yield a colorless oil. The oil was triturated with hexane to yield the title compound as a colorless solid: 8.43 g (28.7 mmol); $R_f=0.26$ (silica gel, benzene:isopropyl ether 85:15).

(C)

(3R)-3-[[(1,1-Dimethylethoxy)carbonyl]amino]-2-[[(4-methoxyphenyl)methyl]thio]benzenebutanoic acid, methyl ester To a 0° C. solution of diisopropylamine (2.1 ml, 15 mmol, 2.2 eg) and anhydrous tetrahydrofuran (20 ml) was added n-butyl lithium (6.0 ml, 14.65 mmol, 2.42 M solution in hexane) and stirring continued for 30 minutes. The reaction was cooled to −78° C. and treated with a solution of (R)-3-[[(1,1-dimethylethoxy)carbonyl]amino]benzenebutanoic acid, methyl ester (2.0 g, 6.81 mmol) and tetrahydrofuran (8 ml). After 15 minutes, the mixture was warmed to −30° C., stirred 15 minutes and the orange solution treated with a solution of p-methoxybenzyl disulfide (2.5 g, 1.2 eq) and tetrahydrofuran (9 ml). After 5 minutes, the reaction was warmed to 0° C. and stirred for 45 minutes. The reaction was then quenched with the addition of 1N hydrochloric acid and diluted with ethyl acetate. The organic phase was washed with water, 1N hydrochloric acid, 1N sodium bicarbonate and brine, dried over anhydrous magnesium sulfate and concentrated to a yellow oil. The oil was chromatographed (flash, silica gel LPS-1, benzene:isopropyl ether 92:8) to yield the title compound as a yellow oil: 2.2 g (4.98 mmol).

(D)

(3R)-3-[[(1,1-Dimethylethoxy)carbonyl]amino]-2-[[(4-methoxyphenyl)methyl]thio]benzenebutanoic acid A mixture of (3R)-3-[[(1,1-dimethylethoxy)carbonyl]amino]-2-[[(4-methoxyphenyl)methyl]thio]benzenebutanoic acid, methyl ester (2.34 g, 5.25 mmol), 1N sodium hydroxide (15.75 ml, 3 eq), distilled water (4.25 ml) and tetrahydrofuran (20 ml) was stirred at room temperature for 18 hours. The reaction was treated with 1N sodium hydroxide (5 ml) and stirring was continued for 12 hours. The reaction was made acidic with the addition of 1N hydrochloric acid, diluted with ethyl acetate and the organic phase washed twice with water and brine. Drying over anhydrous magnesium sulfate and removal of solvent yielded the title compound as an amber oil (1.98 g, 4.59 mmol).

(E)

N-[(3R)-[[(1,1-Dimethylethoxy)carbonyl]amino]-2-[[(4-methoxyphenyl)methyl]thio]-1-oxo-4-phenyl-butyl-L-leucine, 1,1-dimethylethyl ester (Isomers A and B)

A solution of (3R)-3-[[(1,1-dimethylethoxy)carbonyl]amino]-2-[[(4-methoxyphenyl)methyl]thio]benzenebutanoic acid (1.98 g, 4.59 mmol), 2-morpholinoethyl isocyanide (0.63 ml, 1 eq) hydroxybenzotriazole monohydrate (620 mg, 1 eq) and dry dichloromethane (20 ml) was stirred at room temperature under argon for 45 minutes. The yellow reaction mixture was treated with a solution of L-leucine-t-butyl ester (860 mg, 1 eq) and dichloromethane (10 ml) followed by diiso-propylethylamine (0.96 ml, 1.2 eq). After stirring for 20 hours, the reaction mixture was diluted with ethyl acetate and washed with water (twice), 1N hydrochloric acid (twice), 1N sodium bicarbonate (twice) and brine. Drying over anhydrous magnesium sulfate and removal of solvent yielded a yellow semi-solid. This material was chromatographed four times (flash, silica gel LPS-1, benzene:ethyl acetate, 92:8) to yield Isomer B (550 mg, 0.92 mmol). Fractions containing impure Isomer A were combined and chromatographed, as above, to yield the isomer as a colorless solid (550 mg, 0.92 mmol) $R_f=0.35$ Isomer A, $R_f=0.25$ Isomer B (silica gel, benzene:ethyl acetate, 92:8).

(F)

N-[(3R)-3-Amino-2-mercapto-1-oxo-4-phenylbutyl]-L-leucine, monohydrochloride (Isomer A)

A solution of distilled trifluoroacetic acid (14 ml) and anisole (1 ml) was added to N-[(3R)-[[(1,1-dimethylethoxy)carbonyl]amino]-2-[[(4-methoxyphenyl)methyl]thio]-1-oxo-4-phenylbutyl-L-leucine, 1,1-dimethylethyl ester (Isomer A, 480 mg, 0.80 mmol) and stirred at room temperature for 1.5 hours. The reaction was cooled to 0° C. and treated with mercuric trifluoro-acetate (375 mg, 1.1 eq) and stirred 1 hour at 0° C. The reaction was concentrated to a red oil and taken into a minimal amount of ether. Hexane was added to form a precipitate. The solid was collected, washed with hexane and dried under argon to yield 528 mg of a nearly colorless solid. This material was taken into 80% aqueous acetic acid (20 ml) and gassed with hydrogen sulfide for 20 minutes. The black reaction mixture was filtered through a pad of Celite followed by millipore (teflon). The filtrate was concentrated to an oil and diluted with degassed double distilled water and 1N hydrochloric acid (1.2 ml, 1.5 eq). The resulting mixture was filtered (millipore, Metricel) and the clear colorless filtrate lyophilized three times to yield the title compound as a fluffy colorless solid (280 mg, 0.77 mmol); $R_f=0.73$ (silica gel, n-butanol:acetic acid:water, 3:1:1); fast atom bombardment; mass spectrum $(M+H)^+m/e=325$, $(M-H)^-m/e=323$, melting point 94°–106° C.

Analysis Calc'd: $C_{16}H_{24}N_2O_3S.1M$ hydrochloric acid.1 M water: C, 50.57; H, 6.86; N, 7.46; S, 8.31; SH, 8.44; Cl, 9.15. Found: C, 50.72; H, 7.18; N, 7.39; S, 8.46; SH, 8.73; Cl, 9.36.

EXAMPLE 3

N-[(3R)-3-Amino-2-mercapto-1-oxo-4-phenylbutyl]-L-leucine, monohydrochloride (Isomer B)

A solution of distilled trifluoroacetic acid (14 ml) and anisole (1 ml) was added to N-[(3R)-[[(1,1-dimethylethoxy)carbonyl]amino]-2-[[(4-methoxyphenyl)methyl]-thio]-1-oxo-4-phenylbutyl-L-leucine, 1,1-dimethylethyl ester (Isomer B), (500 mg, 0.83 mmol; see example 2E) and stirred at room temperature for 1 hour. The reaction was cooled to 0° C. and treated with mercuric trifluoro-acetate (390 mg, 1.1 eq) and stirred at 0° C. for one hour. The reaction was concentrated to an amber oil and ether was added causing a precipitate to form. Hexane was added to the mixture and the solid was triturated then collected. Washing with hexane and drying under argon yielded 550 mg of a nearly colorless solid. This material was taken into 80% aqueous acetic acid (20 ml) and gassed with hydrogen sulfide for 20 minutes. The black reaction mixture was filtered through Celite then millipore (teflon). The filtrate was concentrated and diluted with degassed double distilled water and 1N hydrochloric acid (1.25 ml, 1.5 eq). The resulting mixture was filtered (millipore, Metricel) and the clear, colorless filtrate lyophilized three times to yield the title compound as a fluffly colorless solid (250 mg, 0.69 mmol); $R_f=0.81$ (silica gel, n-butanol:acetic acid:water, 3:1:1); fast atom bombardment mass spectrum: $(M+H)m/e=325$, $(M-H)m/e=323$; melting point 89°–97° C.

Analysis Calc'd.: $C_{16}H_{24}N_2O_3.0.9$ M hydrochloric acid.0.15 M trifluoroacetic acid.0.9 M water: C, 50.13; H, 6.93; N, 7.17; S, 8.21; SH, 8.47; Cl, 8.17; F, 2.19. Found: C, 50.36; H, 6.74; N, 7.06; S, 8.12; SH, 8.38; Cl, 8.35; F, 2.50.

Additional compounds falling within the scope of this invention are compounds having the formula

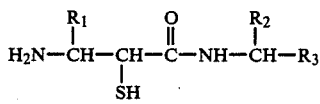

wherein the substituents are as defined below:

| | $R_1$ | $R_2$ | $R_3$ |
|---|---|---|---|
| 1. | $-CH_3$ | $-CH_2-CH(CH_3)_2$ | $-C(=O)-OH$ |
| 2. | $-(CH_2)_4-NH_2$ | $-CH_2-CH(CH_3)_2$ | $-C(=O)-NH_2$ |
| 3. | $-(CH_2)_3-NH-C(=NH)-NH_2$ | $-CH_2-$phenyl | $-C(=O)-NH_2$ |
| 4. | $-CH_2-C(=O)-OH$ | $-CH_2-CH(CH_3)_2$ | $-C(=O)-OH$ |
| 5. | $-CH_2-CH_2-C(=O)-OH$ | $-CH_2-$phenyl | $-C(=O)-NH_2$ |
| 6. | $-CH_2-$(thiophene) | $-CH_2-CH(CH_3)_2$ | $-C(=O)-OH$ |
| 7. | $-CH_2-$phenyl | $-(CH_2)_4-NH_2$ | $-C(=O)-NH_2$ |
| 8. | $-CH_2-$phenyl | $-(CH_2)_3-NH-C(=NH)-NH_2$ | $-C(=O)-OH$ |
| 9. | $-CH(CH_3)_2$ | $-CH_2-CH(CH_3)_2$ | $-H$ |
| 10. | $-CH_2-OH$ | $-CH_2-$phenyl | $-H$ |

-continued

| R₁ | R₂ | R₃ |
|---|---|---|
| 11. —CH₂—OH | —CH₂—C₆H₅ | —C(O)—NH₂ |
| 12. —CH₂—SH | —CH₂—CH(CH₃)₂ | —C(O)—OH |
| 13. —CH₂—CH₂—S—CH₃ | —CH₂—C₆H₅ | —H |
| 14. —CH₂-(3-indolyl) | —CH₃ | —C(O)—NH₂ |
| 15. —H | —CH₂—C₆H₅ | —C(O)—OH |
| 16. —CH₂—C₆H₄—OH | —H | —C(O)—NH₂ |
| 17. —CH₂—C₆H₄—OH | —CH₃ | —H |
| 18. —CH₂-(imidazolyl) | —CH₂—CH(CH₃)₂ | —C(O)—OH |
| 19. —CH(OH)—CH₃ | —CH₂—C₆H₅ | —H |

What is claimed is:

1. A compound having the formula

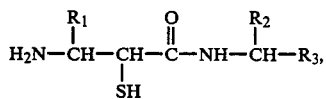

or a pharmaceutically acceptable salt thereof wherein $R_1$ and $R_2$ are each independently hydrogen, alkyl, carboxyalkyl, halo-substituted alkyl, hydroxyalkyl, aminoalkyl, mercaptoalkyl, alkylthioalkyl, (cycloalkyl)alkyl, (heteroaryl)alkyl, arylalkyl, carbamoylalkyl, guanidinyl-alkyl or heteroaryl;

$R_3$ is hydrogen, alkyl, cycloalkyl, aryl, heteroaryl, arylalkyl, (heteroaryl)alkyl,

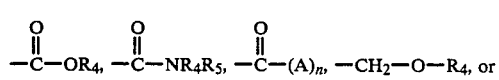

—continued

—CH₂—NR₄R₅;

$R_4$ and $R_5$ are each independently hydrogen, alkyl, cycloalkyl, aryl, heteroaryl, arylalkyl, or (heteroaryl)alkyl;

A is glycyl, alanyl, leucyl, phenylalanyl, arginyl, sarcosyl, seryl, asparagyl, lysyl, glutamyl, histidyl, tryptophyl, cysteinyl, methionyl, threonyl, tyrosyl, valyl, aspartyl, prolyl, norleucyl, or norvalyl; and n is an integer of 1 to 6;

wherein the term "aryl" refers to phenyl or phenyl substituted with 1, 2 or 3 alkyl, alkoxy, alkylthio, hydroxy, chlorine, bromine, fluorine, amino, alkylkamino, dialkylamino, nitro or trifluoromethyl groups;

the terms "heteroary", "alkyl" and "alkoxy" refer to groups having 1 to 7 carbon atoms; and the term "cycloalkyl" refers to groups having 3, 4, 5, 6 or 7 carbon atoms.

2. A compound in accordance with claim 1 wherein $R_1$ is phenylmethyl.

3. A compound in accordance with claim 1 wherein $R_2$ is alkyl.

4. A compound in accordance with claim 1 wherein $R_2$ is 2-methylpropyl.

5. A compound in accordance with claim 1 wherein $R_3$ is

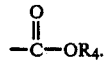

6. A compound in accordance with claim 5 wherein $R_4$ is hydrogen.

7. The compound in accordance with claim 1, N-[(3S)-3-amino-2-mercapto-1-oxo-4-phenylbutyl]-L-leucine, or a pharmaceutically acceptable salt thereof.

8. The compound in accordance with claim 1, N-[(3R)-3-amino-2-mercapto-1-oxo-4-phenylbutyl]-L-leucine, or a pharmaceutically acceptable salt thereof.

9. The compound in accordance with claim 1, N-[(3R)-3-amino-2-mercapto-1-oxo-4-phenylbutyl]-L-leucine, or a pharmaceutically acceptable salt thereof.

* * * * *